United States Patent [19]

Singh et al.

[11] Patent Number: 5,420,157
[45] Date of Patent: May 30, 1995

[54] INHIBITORS OF FARNESYL PROTEIN TRANSFERASE OR PRODRUGS THEREOF

[75] Inventors: Sheo B. Singh, Edison; Gerald F. Bills, Roselle; Russell B. Lingham, Watchung; Keith C. Silverman, Somerset; Deborah L. Zink, Manalapan, all of N.J.

[73] Assignee: Merck & Co., Inc., Rahway, N.J.

[21] Appl. No.: 808,124

[22] Filed: Dec. 16, 1991

[51] Int. Cl.$^6$ ............... A01N 43/32; C07D 307/02; C07D 307/34

[52] U.S. Cl. ............... 514/452; 549/261; 549/413; 549/477

[58] Field of Search ............... 514/452; 549/479, 413, 549/477, 261; 435/123, 142, 193

[56] References Cited

U.S. PATENT DOCUMENTS

| | | | |
|---|---|---|---|
| 3,017,417 | 1/1962 | Harkes | 549/261 |
| 3,155,685 | 11/1964 | Prill et al. | 549/313 |
| 4,874,782 | 10/1989 | Bonjouklian et al. | 549/313 |
| 5,043,268 | 8/1991 | Stock . | |

FOREIGN PATENT DOCUMENTS

| | | | |
|---|---|---|---|
| 0456180A1 | 11/1991 | European Pat. Off. | C12N 9/10 |
| WO91/16340 | 10/1991 | WIPO | C07K 7/06 |

OTHER PUBLICATIONS

Gill, M. "3-[(7Z)-hexadecenyl]-4-metholfuran-2,5-dione from Piptoporus australiensis.", Phytochemistry, 21:1786-1788 (1982).

Turner, W. B., et al., "Secondary Metabolites Derived from Intermediates of the Tricarboxylic Acid Cycle", *Fungal Metabolites II*, Academic Press, pp. 367-383 (1983).

Biller, S. A., "The First Potent Inhibitor of Squalene Synthase: A Profound Contribution of an Ether Oxygen to Inhibitor—Enzyme Interaction", J. Am. Chem. Soc., 113, 8522-8524 (1991).

Goldstein, J. L., et al., "Nonfarnesylated Tetrapeptide Inhibitors of Protein Farnesyltransferase", *The Journal of Biological Chemistry*, vol. 266, No. 24 pp. 15575-15578 (1991).

Chemical Abstract, vol. 108, No. 7760e, Urushibata et al, 1988 "Sizing emsulions for paper".

A. Selva et al., New Secondary Metabolites of Aspergillus Wentii Wehmer; Biomed. Mass Spectrom., 7, 148-152 (1980).

*Primary Examiner*—C. Warren Ivy
*Assistant Examiner*—Raymond Covington
*Attorney, Agent, or Firm*—David A. Muthard; Mark R. Daniel; Joseph F. DiPrima

[57] ABSTRACT

This invention relates to pharmaceutical compounds of structural formulae (I) and (II):

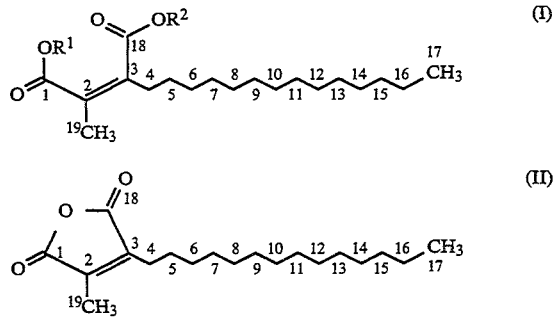

and compositions and methods of treatment utilizing these compounds to inhibit farnesyl protein transferase and farnesylation of the oncogene protein Ras.

7 Claims, No Drawings

INHIBITORS OF FARNESYL PROTEIN TRANSFERASE OR PRODRUGS THEREOF

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171-286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093-1098 (1989); Hancock et al., *Cell* 57:1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell,* 62:81-88 (1990); Schaber et al., *J. Biol. Chem.,* 265:14701-14704 (1990); Schafer et al., *Science,* 249:1133-1139 (1990); Manne et al., *Proc. Natl. Acad. Sci USA,* 87: 7541-7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630-6634(1989)). Cytosol-localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid; Reiss et. al., ibid; Reiss et al., *PNAS,* 88:732-736 (1991)). However, the reported inhibitors of farnesyl-transferase are metabolically unstable or inactive in cells.

It has further been reported in the art that a structure of a new citraconic anhydride derivative from *Piptoporus australiensis* has been established by spectroscopic and chemical methods as 3-[(7Z)-hexadecenyl]-4-methylfuran-2,5-dione, (M. Gill, *Phytochemistry,* 21:1786-1788 (1982).

It is, therefore, an object of this invention to develop pharmaceutical compounds and compositions and methods utilizing the compounds of this invention to inhibit farnesyl-protein transferase and farnesylation of the oncogene protein Ras.

SUMMARY OF THE INVENTION

The present invention relates to pharmaceutical compounds of structural formulae (I) and (II):

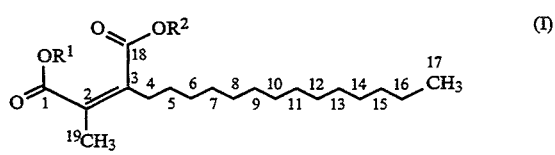

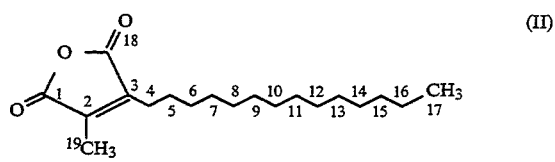

and pharmaceutical compositions and methods of treatment utilizing these compounds to inhibit farnesyl-protein transferase and farnesylation of the oncogene protein Ras.

DETAILED DESCRIPTION OF THE INVENTION

The present invention is directed to pharmaceutical compounds of structural formula (I) which are inhibitors of farnesyl-protein transferase and farnesylation of the oncogene protein Ras:

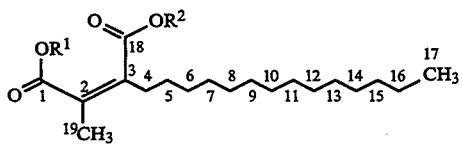

wherein:
$R^1$ and $R^2$ are each independently selected from:
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt of a compound of formula (I) in which at least one of $R^1$ and $R^2$ is hydrogen;

when $R^1$, $R^2$ is other than H these compounds may not be inhibitors of farnesyl protein transferase but may act as prodrugs;

A second embodiment of the present invention 5 is the compound of formula II which is shown below:

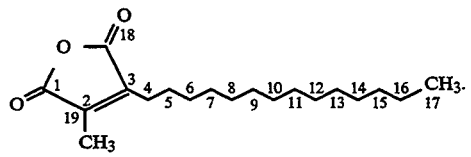

Throughout this specification and claims, the olefin configuration of the 2,3-olefin is as shown.

A preferred compound (9) of this invention is set forth below:

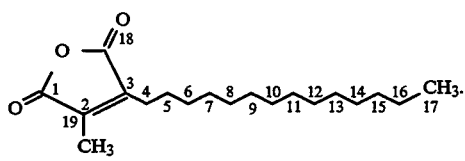

A second preferred compound (10) of this invention is set forth below:

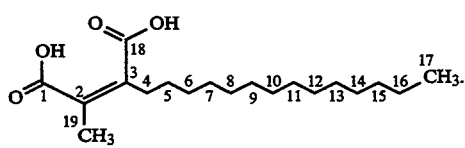

The compounds (9) and (10) are prepared in an aerobic fermentation procedure employing a novel culture, MF5685, identified as *Chaetomella acutiseta*. Although the use of this organism is specifically described herein, other organisms of the genus Chaetomella including mutants of the above described organism are also capable of producing compounds of this invention.

The culture MF5685 is that of a fungus, *Chaetomella acutiseta*, isolated from a decaying fruiting body of *Phillinus robinae* growing parasitically on *Robinia pseudoacacia* in Sussex County, N.J. This culture has been deposited under the terms of the Budapest Treaty with the American Type Culture Collection at 12301 Parklawn Drive, Rockville, Md. 20852 as ATCC 74113.

The culture MF5685, identified as *Chaetomella acutiseta* exhibits the following morphological features.

Colonies on oatmeal agar (Difco Laboratories) 20° C., 95% relative humidity, 12 hr photoperiod under fluorescent light, attaining a diameter of 40–42 mm in 3 weeks, slightly raised, densely felty to almost wooly, dull, distinctly white at the margin, but soon pale buff to pinkish buff or pale brown, near Tilleul-Buff (capitalized color names from Ridgway, R. 1912. Color Standards and Nomenclature, Washington, D.C.), Vinaceous-Buff, Avellaneous, with dense aggregations of brown to dark brown, Carob Brown, conidiomata developing in irregular concentric zones, with margin minutely fimbriate or plumose, reverse mottled buff to vinaceous brown or brown. Odors and exudates absent.

Colonies on malt yeast extract agar (Difco Laboratories) 20° C., 95% relative humidity, 12 hr photoperiod under fluorescent light, attaining a diameter of 40–41 mm in 3 weeks, slightly raised, densely felty, faintly radially plicate, white to pale pinkish buff to grayish pink-buff, Pale Cinnamon-Pink, Pale Pinkish Cinnamon, Light Pinkish Cinnamon, to Avellaneous, with scattered dark brown, Carob Brown, conidiomata, with margin even submerged, reverse pale buff-yellow to pinkish yellow. Odors and exudates absent.

Colonies on cornmeal agar (Difco Laboratories) 20° C., 95% relative humidity, 12 hr photoperiod under fluorescent light, attaining a diameter of 28–29 mm in 3 weeks, appressed, translucent, with no aerial mycelium, with scattered dark brown conidiomata forming on the agar surface, with margin irregular, submerged, reverse translucent. Odots and exudates absent.

Conidiomata 300–700 μm in diameter, 200–500 μm tall, subglobose, ellipsoidal, reniform in side view, usually bilaterally symmetrical and somewhat laterally compressed, sessile or with a slight basal pedicel, consisting of two opposing shell-like peridia, dehiscing at a central suture or raphe between the two peridia, with outer walls setose, with peridial wall composed of isodiametric to slightly elongated cells, with outer layers of cells dark brown, inner layers hyaline. Setae of peridium lanceolate, 90–200 μm long. 5–10 μm wide at midpoint, smooth-walled, thick-walled, 4–10 septate, pale to dark brown. Conidiophores lining the basal region of conidiomatal cavity, most abundant directly above the pedicel, hyaline, branched, 12–30 μm tall. Conidiogenous cells enteroblastic, phialidic, hyaline, filiform, with a minute pore at conidiogenous locus. Conidia hyaline, smooth, aseptate, fusiform to subfalcate, 8.5–11.5×1-.8–2.2 μm.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 22 days, without agitation. The fermentation is conducted aerobically at temperatures ranging from 20° to 40° C. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound(s) isolated.

A mixture of an alcoholic solvent and an oxygenated solvent, such as an ester or a ketone, is employed to extract a compound(s) of this invention from the solid fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is a 1:1 mixture of methanol and 2-butanone. After concentrating the initial extract and diluting with water, the preferred partitioning solvent is dichloromethane.

The chromatographic separations may be carried out by employing conventional column chromatography with ionic or nonionic absorbents or resins. Silica gel, such as that available from E. Merck, is the preferred adsorbent. When silica gel is the adsorbent, an alcohol/-chlorohydrocarbon/organic acid mixture such as methanol/chloroform/acetic acid/water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 ($Cl^-$) or Dowex-50 ($Ca^{++}$) are also useful in the purification.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, or both of the carboxyl groups are in the salt form.

The intrinsic farnesyl-protein transferase (FTase) activity of representative compounds of this invention was measured by the assay as described below:

Farnesyl-protein transferase (FTase) from bovine brain was chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS (Cys-Val-Leu-Ser) at 3.5 μM, 0.25 μM [$^3$H]FPP, and the indicated compounds were incubated with this partially purified enzyme preparation. The FTase inhibition data presented below is a measurement of the ability of the test compound to inhibit Ras farnesylation in vitro.

TABLE 1

| Inhibition of Ras farnesylation by representative compound of this invention | |
|---|---|
| Compound | $IC_{50}$ (nM) |
| (9) or (10) | 46 |

The pharmaceutical compositions containing the compounds of structural formula I and II inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

The compounds of this invention may also be prepared according to the reaction scheme as set forth below:

Aldol condensation of methyl palmitate (1) with methyl pyruvate at −78° C. to room temperature gave the diastereomeric mixture of (2) and (3) which was separated. Tosylation of the tert hydroxyl group gave (4) and (5) which upon β-elimination using DBU yielded the olefins. The elimination products, (6), (7) and (8), were isolated by silica gel chromatography. The methyl esters were hydrolyzed by refluxing with aqueous sodium hydroxide in methanol-THF mixture. Hydrolysis of diester (6) followed by acidification gave (9) which was converted to (10) in methanol water (8:2) at pH 7.0 to 7.2.

REACTION SCHEME

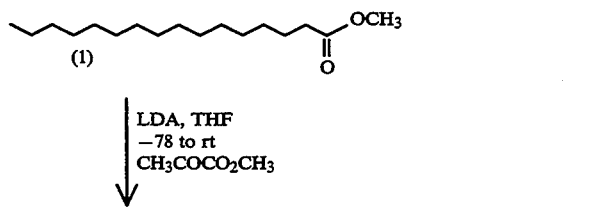

-continued
REACTION SCHEME

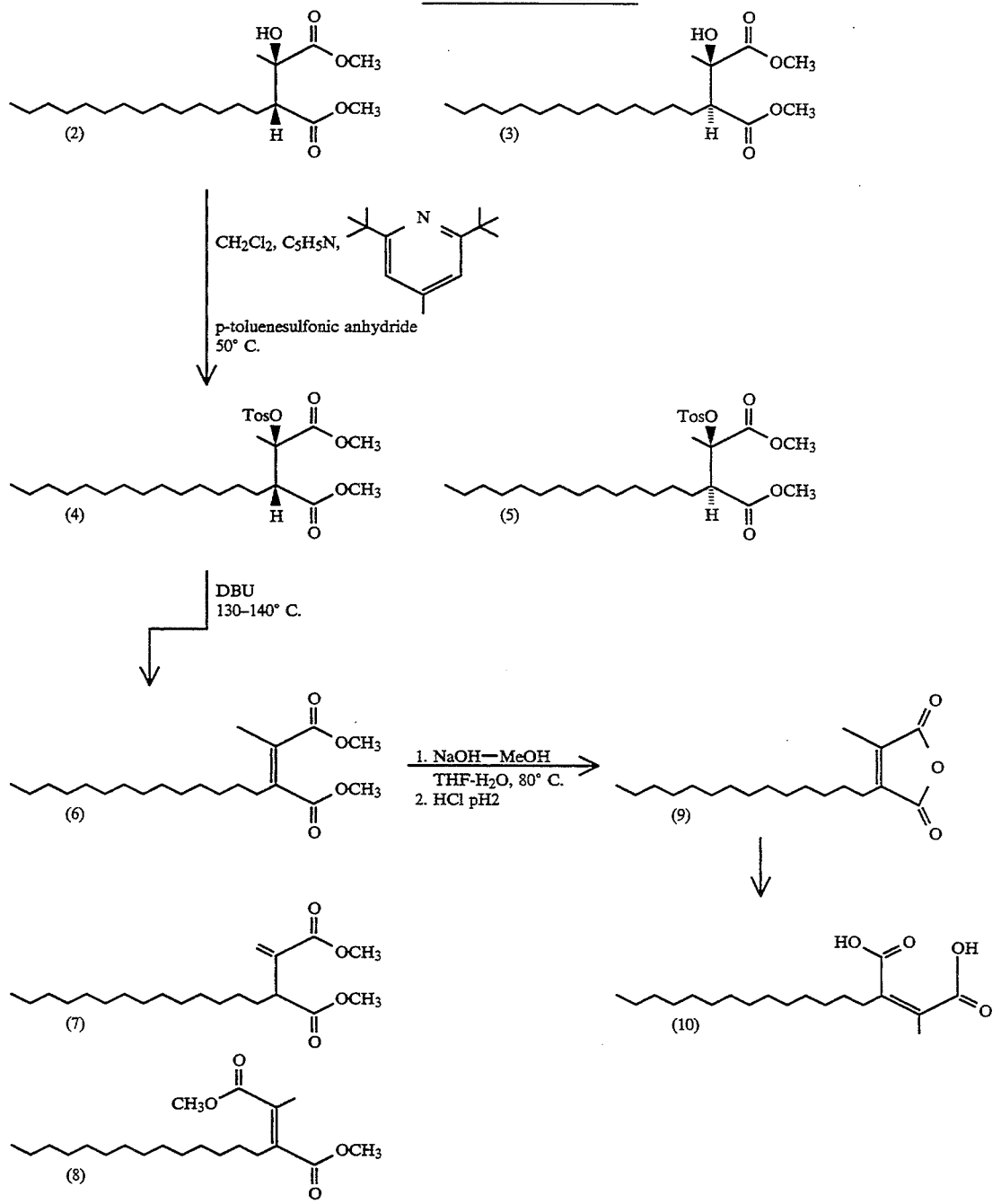

The equilibrium between diacid (10) and anhydride (9) in a solution is pH dependent. The anhydride (9) predominates when the solution is acidic, however, the diacid (10) predominates when the solution is basic as exemplified below: UV spectrum of (9) in CH₃CN showed a maximum for cyclic anhydride at 254 nm which did not change by addition of dil HCl. However, when basified with dil NaOH, this maximum shifted to $\lambda$max 243 nm. This shift is clear evidence of opening of the anhydride into the diacid. The UV spectrum of synthetic trans diacid showed a $\lambda$max at 239 nm.

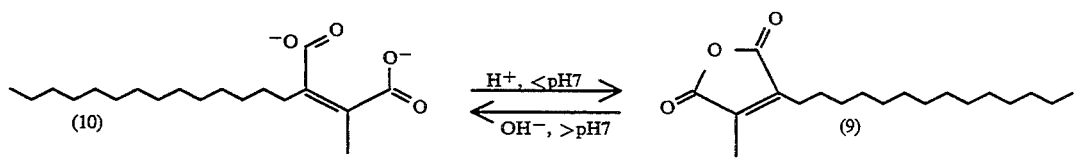

The UV spectrum of (9) recorded in the CH₃OH-HEPES buffer solution (7:5, methanol was needed to make a clear solution) at pH 7.5 (buffer and pH used for Ras farnesyl-protein transferase assay) showed UV maximum at 243 nm. This indicates that under assay conditions the compound (9) exits in the open dicarboxylate form of compound (10). The UV spectrum in neat $CH_3OH$ exhibited two maxima: 211 and 253 nm. The latter band under went a hypsochromic shift to 240 nm after addition of dil NaOH. The anhydride (9) reacts slowly with $CH_3OH$ (a methanolic solution of anhydride (9) gave the dimethyl ester (6) after reacting with $CH_2N_2$). The open diacid form (10) was trapped as a diisopropylethylamine salt without any loss of RAS farnesyl transferase inhibitory activity.

The composition of media employed in the following Examples are listed below:

|  | g/L |
| --- | --- |
| MYE Agar Medium: | |
| Malt extract | 10.0 |
| Yeast extract | 2.0 |
| Agar | 20.0 |
| 2% dieldrin* | 1.0 ml |
| pH not adjusted | |
| autoclave 20 minutes | |
| (121 C., 15 psi) | |
| * = g/100 mls acetone | |
| Velsicol Chemical Corporation | |
| Chicago, Illinois | |
| KF SEED MEDIUM: | |
| Tomato paste | 40.0 |
| Corn steep liquor | 5.0 |
| Oat Flour | 10.0 |
| Cerelose | 10.0 |
| *Trace elements #2 | 10.0 mls |
| pH adjusted to 6.8 (presterile) | |
| 50 mls/nonbaffled 250 mls | |
| Erlenmeyer flask | |
| autoclave 20 minutes (121 C., 15 psi) | |
| dissolved in 1 L 0.6 N HCl | |
| *Trace Elements #2 | |
| $FeSO_4.7H_2O$ | 1.0 |
| $MnSO_4.4H_2O$ | 1.0 |
| $CuCl_2.2H_2O$ | 0.025 |
| $CaCl_2.2H_2O$ | 0.1 |
| $H_3BO_3$ | 0.056 |
| $(NH_4)_6Mo_7O_{24}.4H_2O$ | 0.019 |
| $ZnSO_4.7H_2O$ | 0.2 |

Production Media
Solid Substrate Production Media
solid substrate media prepared in nonbaffled
250 mls Erlenmeyer flasks

| BRF | |
| --- | --- |
| Brown rice | 10.0 g/flask |
| Base liquid #3 | 20.0 mls/flask |
| Base liquid #3 | |
| Yeast extract | 1.0 |
| Sodium tartrate | 0.5 |
| $KH_2PO_4$ | 0.5 |
| distilled $H_2O$ | 1000 mls |
| no pH adjustment | |
| autoclave 15 minutes (121 C., 15 psi) | |
| add 15.0 mls distilled $H_2O$/flask | |
| autoclave 20 minutes (121 C., 15 psi) | |

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of Compounds of (9) and (10) by Fermentation

A. Culturing MF 5685

Culture MF 5685 was inoculated into KF seed medium using a mixture of hyphae and spores transferred from growth on a MYE agar slant. KF seed flasks were incubated for 67 hours at 25° C., 220 rpm, 85% humidity. At the end of this incubation, KF flasks were pooled and 2.0 mls aliquots were aseptically transferred to each of 40 BRF solid production medium flasks. These production flasks were then incubated statically at 25 C., 85% humidity for 9 days (20 flasks) or 16 days (16 flasks). At harvest 75 mls of methyl ethyl ketone (MEK) were added to each production flask and the solid growth was manually broken apart into smaller pieces. Solvent treated flasks were placed onto a gyrotory shaker for agitation at 220 rpm for 30 minutes in order to further break apart the mycelial mass as well as to improve contact of the solvent with the cells.

B. Isolation of Compounds (9) and (10)

One liter (20 flasks) fermentation of *Chaetomella acutiseta* grown on BRF solid medium was extracted with methyl ethyl ketone (MEK, 1.5 L) by shaking for 20 minutes as described above. The extract was filtered through celite and mycelia was washed with 75 ml each with MEK to give an extract of total volume (3.0 L). Filtrate was concentrated to dryness under reduced pressure. The residual semisolid material was suspended in methanol (55 mL) and filtered. The filtrate (55 mL) was chromatographed on a 2.0 L Sephadex LH-20 column in methanol. Two RAS farnesyl transferase active fractions were obtained. These fractions were suspended separately in methanol (4 mL each) and centifugated to remove solid material. One mL aliquot of methanolic supernatant was subsequently chromatographed on a Whatman C-8 (22×250 mm) column using $CH_3CN$ (75%) and $H_2O$ (25% containing 0.25% $H_3PO_4$) at a flow rate of 10 ml/min. At this time it became clear that Ras farnesyl transferase activity was due to two different compounds having retention time 13.2 and 14.2 minutes [Whatman C-8 (4.6×250 mm), $CH_3CN$ (80%)—$H_2O$ (20% containing 0.25% $H_3PO_4$) at a flow rate of 1.5 mL/min] in a ratio of approximately 56:44. The preparative HPLC was repeated seven times. Fractions thus obtained were concentrated to remove most of the $CH_3CN$ and then extracted with ethyl acetate. The ethyl acetate extract was washed once with an equal volume of $H_2O$ and concentrated to dryness to give a first fraction (100 mg) enriched in compound (9) and (10). The ratio of compounds (9) and (10) depends on the pH of solution. This fraction was further chromatographed repeatedly using the same HPLC conditions and fractions were throughly dried under vacuum to give compound (9) (40 mg, ret time 13.2 min) as a wax. Compound of (10) exits in solution at pH 7 and above and could be isolated as a salt from the fractions by first basifying the fractions to pH greater than 7.0 and evaporating the solvents.

Mass Spectral Data

Mass spectra were recorded on a Finnigan-MAT model MAT212 (electron impact, EI, 90 eV), MAT 90 (Fast Atom Bombardment, FAB), and TSQ70B (FAB, EI) mass spectrometers. Exact mass measurements were performed at high resolution (HR-EI) using perfluorokerosene (PKF) or perfluoropolypropylene oxide (Ultramark U1600F) as an internal standard. Trimethyl silyl derivatives were prepared with a 1:1 mixture of BSTFA-pyridine at room temperature.

$^{13}$C NMR Data $^{13}$C NMR spectra were recorded in $CD_2Cl_2$ or $CD_3OD$ or $CDCl_3$ at 75 MHz on a Varian XL-300 spectrometer. Chemical shifts are given in ppm relative to TMS at zero using the solvent peak at 53.8 ppm ($CD_2Cl_2$), 49.00 ppm ($CD_3OD$) and 77.00 ppm ($CDCl_3$) respectively as an internal standard.

$^1$H NMR Data $^1$H NMR spectra were recorded in $CD_2Cl_2$ or $CD_3OD$ or $CDCl_3$ at 300 MHz on a Varian XL-300 spectrometer. Chemical shifts are given in ppm relative to TMS at zero using the solvent peaks at 5.32 ppm ($CD_2Cl_2$), 3.30 ppm ($CD_3OD$) and 7.26 ppm ($CDCl_3$), respectively, as internal standards.

Physical Properties of the compounds (9) and (10)

Mass Spectral Data for Compound (10)

This compound has the molecular weight 326. The molecular formula $C_{19}H_{34}O_4$ was determined by HR-MS measurement of the di-trimethylsilyl derivative (calcd for $C_{19}H_{34}O_4 + C_5H_{13}Si_2$ 455.3012, found 55.3013). A mass spectral ion was obtained at m/z 309 which could be formula I-OH.

Mass Spectral Data for Compound (9)

Thoroughly dried sample has a molecular weight 308. The molecular formula $C_{19}H_{32}O_3$ was determined by HR-MS measurement (calcd for $C_{19}H_{32}O_3$ 308.2351, found 308.2350).

$^1$H NMR Data for Compound (9)

$^1$H NMR Spectrum in $CD_2Cl_2$:2.45 (2H, tq*, J=7.5, 0.8 Hz), 2.05 (3H, brs), 1.56 (2H, m), 1.27 (22H, m), 0.88 (3H, t, J=6.9 Hz)

*after resolution enhancement.

$^{13}$C NMR Data for Compound (9)

$^{13}$C NMR Spectrum in $CD_2Cl_2$: 166.8, 166.4, 45.1,141.0, 32.3, 30.08, 30.05 ($\times$2), 30.03, 29.98, 9.85, 29.78, 29.76, 29.60, 27.93, 24.7, 23.09, 14.3, 9.7.

Infra Red Spectrum for Compound (9)

Dried sample $\nu_{max}$ (ZnSe): 2924, 2854, 1767, 467, 1277, 1118, 923,735 cm$^{-1}$.

Ultraviolet Spectrum for Compound (9)

$\lambda$max (CHCl$_3$): 255 ($\epsilon$=6762) nm.

Ultraviolet Spectrum for Compound (10)

$\lambda$max (CH$_3$OH-HEPES buffer pH 7.5 ): 243 nm.

EXAMPLE 2

Preparation of Compounds (9) and (10) by Synthesis

Step 1

Aldol Condensation of Methyl Palmitate and Methyl Pyruvate (Preparation of (2) and (3))

n-Butyl lithium (1.6M in hexane, 6.6 mL, 10.5 mmol) was added to a cooled (−78° C.) solution of diisopropyl amine (2.2 mL, 15 mmol) in THF (10mL). The solution was stirred under N$_2$ at −78° C. for 10 minutes followed by a0° C. for 10 minutes. After cooling the LDA solution at −78° C., a THF (20mL) solution of methyl palmirate (1) (2.7 g, 10 mmol) was added via a syringe over a 10 minute period and stirring was continued for 10 minutes. The reaction mixture was slowly allowed to warm to 0° C. and stirred for 30 minutes (faint yellow color). Methyl pyruvate (0.90 mL, 10 mmol) was added via a syringe after recooling the reaction mixture at −40° C. and solution was stirred for 1 hr while slowly warming to rt. Progress of the reaction was monitored on TLC (hexane-EtOAc,4:1). Two polar products were formed. Some unreacted methyl palmitate was still present. The mixture was quenched with water at −78° C. and allowed to warm to room temperature, diluted with aqueous citric acid (100 mL) and extracted with ethyl acetate (3$\times$100 mL). EtOAc extract was washed with water (100mL), dried (Na$_2$SO$_4$), and evaporated under reduced pressure to give an oily material which was chromatographed on a flash silica gel (200 cc) column packed in hexane. The column was eluted with 5% EtOAc in hexane to afford 300 mg of the first diastereomer [(2) or (3), HPLC retention time 7.0 min, Whatman ODS-3, C-18 (4.6$\times$250mm), CH$_3$OH—H$_2$O, 92:8, at a flow rate of 1.5 ml/min], 700 mg of mixture and 300 mg of second diasteromer (3) or (2), ret time 6.4 min). Both compounds were obtained as solids. The stereochemical identity of diastereomers (2) and (3) was not determined.

$^1$H NMR spectrum of (2) or (3) (diastereomer with 7.0 min retention time) in CDCl$_3$: 3.75 (3H,s), 3.67 (3H,s), 2.76 (1H,dd, J=10.5, 3.9 Hz), 1.68 (2H,m), 1.41 (3H,s), 1.25 (24H,brm), 0.87 (3H, t, J=6.3 Hz).

$^1$H NMR spectrum of (3) or (2) (diastereomer with 6.4 min. retention time) in CDCl$_3$: 3.79 (3H,s), 3.71 (3H,s), 2.75 (1H,dd, J=11.7, 3.3 Hz), 1.83 (2H,m), 1.42 (3H,s), 1.23 (24H,m), 0.87 (3H,t, J=6.3 Hz).

Step 2

$\beta$-Elimination Reaction of Aldol Products (Preparation of compounds (6), (7) and (8))

To a solution of 160 mg (0.43 mmol) of the diastereomere with retention time 7.0 minutes (2) or (3) obtained in Step 1 above in CH$_2$Cl$_2$ (1.5 mL) and pyridine (1.0mL) was added 2,6-di-tert-butyl-4-methylpyridine (200 mg, 0.97 mmol) followed by p-toluenesulfonic anhydride (570 mg, 1.74 mmol) and the solution was heated at 50° C. under N$_2$ overnight. Progress of the reaction was monitored on TLC (hexane-EtOAc, 85:15). The tosylate** was less polar than starting alcohol. DBU (0.5 mL) was added and the reaction mixture was heated at 130°-140° C. for 3 hrs to give citraconic acid diester (ret time* 8.8 min, 50%), iraconic acid diester analog (ret time* 9.4 min, 40%) and mesaconic acid diester analog (ret time* 9.8 min. 10%).

**$^1$H NMR spectrum of (4) or (5) in CDCl$_3$: 7.76 (2H,d, J=8.4 Hz), 7.32 (2H,d, J=8.4 Hz), 3.83 (3H, s), 3.67 ( 3H, s), 2.95 (1H, dd, J=11.7, 3.0 Hz), 2.44 (3H,s), 1.81 (3H,s), 1.60 (2H,m), 1.24 (24H,m), 0.88 (3H,t,J=6.6 Hz).

*HPLC condition, What man ODS-3 (C-18), 4.6$\times$250 mm, CH$_3$OH—H$_2$O (92:8), flow rate 1.5 ml/min.

Similarly, reaction of (3) or (2) (diastereomer with retention time 6.4 min) (90 mg, 0.26 mmol) in CH$_2$Cl$_2$ (1.5 mL), pyridine (1mL), 2,6-di-tert-butyl-4-methylpyridine (100 mg) with p-toluenesulfonic anhydride (270 mg) at 50° C. followed by heating with DBU for 20 min gave mesaconic acid diester with citraconate and itaconate dimethyl esters.

Both reaction mixtures were cooled to room temperature and worked up together, they were poured on to EtOAc (200 mL) and washed sequentially with 4N aqueous HCl (3$\times$50 mL), water, 10% aqueous NaHCO$_3$ (3$\times$50 mL) followed by water. The ethyl acetate extract was dried (Na$_2$S)$_4$), evaporated under reduced pressure and crude product was chromatographed on a flash silica gel column (100 cc) packed in hexane and eluted with intially 2% EtOAc followed by 3% to give, citraconate analog (6) (80 mg), (7) (88 mg) and (8) (25 mg). Combined yield 81%.

The tosylate could be purified on the silica gel column using 2 to 5% EtOAc in hexane. The mixture of aldol products could be used for the elimination reaction without any significant problem.

$^1$H NMR spectrum of (6) in CDCl$_3$: 3.75 (3H,s), 3.74 (3H,s), 2.32 (2H,t, J=7.2 Hz), 1.94 (3H,brs), 1.43 (2H,m), 1.24 (22H,m), 0.86 (3H, t, J=6.6 Hz).

$^1$H NMR spectrum of (8) in CDCl$_3$: 3.78 (3H,s), 3.77 (3H,s), 2.43 (2H,t, J=8.5 Hz), 1.99 (3H, brs), 1.40 (2H,m), 1.24 (22H,m), 0.87 (3H,t,J=6.8 Hz).

$^1$H NMR spectrum of (7) in CDCl$_3$: 6.35 (1H,s), 5.74 (1H,s), 3.76 (3H,s), 3.67 (3H,s), 3.49 (1H,t,J=7.2 Hz), 1.86 (1H,M), 1.65 (1H,m), 1.24 (24H,m), 0.87 (3H,t,J=6.3 Hz).

Step 3

Hydrolysis of Citraconate Dimethyl Esters Analog (6) (Preparation of Compound (9))

A solution of citraconate dimethyl ester analog (6) (40mg) in THF (1 mL), methanol (1 mL), water (1 mL) and 4N NaOH (0.5 mL) was heated at reflux overnight and the progress of the reaction was monitored on HPLC*. After completion of the reaction it was cooled to 0° C. and acidified with 4N HCl to pH2. The product was extracted with dichloromethane (2×25 mL). The CH$_2$Cl$_2$ solution was washed with water, dried (Na$_2$SO$_4$) and evaporated to give colorless product anhydride (ret time, 8.9 min) which soidified upon cooling. This product was identical with compound of Formula (II) (HPLC, NMR).

Anal HPLC condition: Whatman C-18, 4.6×250 mm, CH$_3$CN—H$_2$O, 90:10 (containing 0.2% TFA), flow rate 1.5 ml/min.

EXAMPLE 3

As a specific embodiment of an oral composition of a compound of this invention, 20 mg of compound (9)or (10) is formulated with sufficient finely divided lactose to provide a total amount of 580 to 590 mg to fill a size 0 hard gelatin capsule.

EXAMPLE 4

Preparation of an Ammonium Salt

A 0.1 mmol sample of the free acid (10) is dissolved in 10 ml of ethyl acetate. The resulting solution is saturated with gaseous ammonia and evaporated to leave the ammonium salt.

EXAMPLE 5

Preparation of a Potassium Salt

A solution of 0.1 mmol of the free acid of compound (9) or (10) in 10 ml of 6:4 methanol/water is treated with an aqueous or methanolic solution containing 0.2 mmol of potassium hydroxide. Evaporation of the solvent affords the di-potassium salt. Addition of between 0.1 and 0.2 mmol of potassium hydroxide yields analogously mixtures of the mono-potassium and di-potassium and salts whose composition depends upon the exact amount of potassium hydroxide added.

In a similar fashion the sodium and lithium salts can be formed.

EXAMPLE 6

Preparation of a Calcium Salt

A solution of 0.1 mmol of the free acid of compound (9) or (10) in 20 ml of 6:4 methanol/water is treated with an aqueous solution of 0.1 mmol of calcium hydroxide. The solvents are evaporated to give the corresponding calcium salt.

EXAMPLE 7

Preparation of an Ethylenediamine Salt

A solution of 0.1 mmol of the compound (9) or (10) in 10 ml of 6:4 methanol/water is treated with 0.1 mmol of ethylenediamine. Evaporation of the solvent affords the ethylenediamine salt.

The procedure can also be applied to the preparation of the N,N''-dibenzylethylenediamine salt.

EXAMPLE 8

Preparation of a Tris(hydroxymethyl)aminomethane Salt

To a solution of 0.1 mmol of the compound (9) or (10) in 10 ml of 6:4 methanol/water is added from 0.1 to 0.2 mmol of tris(hydroxymethyl)aminomethane dissolved in 10 ml of methanol. Evaporation of the solvent gives a corresponding salt lo form of compound (10), the exact composition of which is determined by the molar ratio of amine added. Similarly prepared are the salts of L-ornithine, L-lysine, and N-methylgluacamine.

EXAMPLE 9

Preparation of an L-arginine Salt

A solution of 0.1 mmol of the free acid (10) or the anhydride (9) in 10 ml of 6:4 methanol/water is treated with an aqueous solution of 0.1 to 0.2 mmol of L-arginine. Evaporation of the solvent affords the title salt, the exact composition of which is determined by the molar ratio of amino acid to the free acid of (10) or the anhydride (9). Similarly prepared are the salts of L-ornithine, L-lysine and N-methylglucamine.

EXAMPLE 10

Preparation Of Dimethyl Ester

To a 5 mg solution of compound with (9) or (10) in methylene chloride (1 mL) and methanol (0.2 mL) was added a 1 mL hexane solution of trimethylsilyldiazomethane. The yellow solution was stored in a refrigerator overnight and then solvent evaporated under stream of nitrogen and filtered through a pipette filled with silica gel and eluted with 2% methanol in methylene chloride to give 4.9 mg of dimethyl ester as a wax.

Mass Spectrum m/z 354; $^1$H NMR spectrum in CDCl$_3$: 3.75 (3H,s), 3.74 (3H,s), 2.32 (2H,t,J=7.2 Hz), 1.94 (3H, brs), 1.43 (2H, m), 1.24 (22H, m), 0.86 (3H, t, J=6.6 Hz); IR spectrum $\nu_{max}$ (ZnSe): 2924, 2854, 1725, 1645, 1466, 1435, 1379, 1264, 1196, 1163, 1125, 1099, 1041, 952,861,770,721 cm$^{-1}$.

What is claimed is:

1. The compound of structural formula (I)

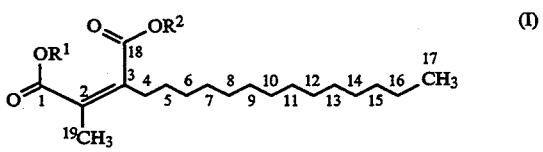

wherein:
R$^1$ and R$^2$ are each independently selected from
a) H;
b) C$_{1-5}$alkyl;
c) C$_{1-5}$alkyl substituted with a member of the group consisting of:

i) phenyl, ii) phenyl substituted with methyl, methoxy, halogen (Cl, Br, F, I) or hydroxy; or a pharmaceutically acceptable salt of a compound of formula (I) in which at least one of $R^1$ and $R^2$ is hydrogen;

when R1, R2 is other than H, these compounds may not be inhibitors of farnesyl protein transferase but may act as prodrugs.

2. The compound of structural formula (II)

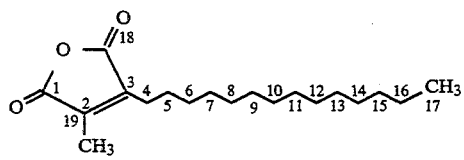
(II)

3. The compound according to claim 1 which

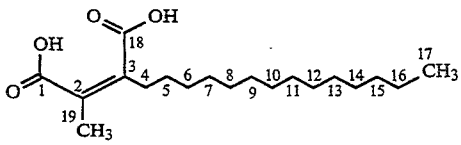

4. A pharmaceutical composition comprising a therapeutically effective amount of a compound of claim 1 and a pharmaceutically acceptable carrier.

5. A pharmaceutical composition comprising a therapeutically effective amount of a compound of claim 2 and a pharmaceutically acceptable carrier.

6. The compound according to claim 1 which is prepared by the process which comprises fermentation of *Chaetomella acutiseta* and isolation of said compound from the fermentation.

7. The compound according to claim 2 which is prepared by the process which comprises fermentation of *Chaetomella acutiseta* and isolation of said compound from the fermentation.

* * * * *